(12) United States Patent
Matulevich

(10) Patent No.: US 6,843,965 B2
(45) Date of Patent: Jan. 18, 2005

(54) AIR FRESHENER SPORTS FIGURE FAN FOR AIR VENTS

(76) Inventor: Jeffrey B. Matulevich, 68 Arbor Oaks Dr., Sarasota, FL (US) 34232

(*) Notice: Subject to any disclaimer, the term of this patent is extended or adjusted under 35 U.S.C. 154(b) by 0 days.

(21) Appl. No.: 10/822,467

(22) Filed: Apr. 12, 2004

(65) Prior Publication Data

US 2004/0235410 A1 Nov. 25, 2004

Related U.S. Application Data

(63) Continuation-in-part of application No. 10/443,333, filed on May 22, 2003, now Pat. No. 6,764,656.

(51) Int. Cl.[7] .................................................. A62B 7/08
(52) U.S. Cl. ...................... 422/124; D23/367; 454/157; 446/124
(58) Field of Search .......................... 454/157; D23/324, D23/367; 40/421, 422; 422/123, 124; 446/199, 201; 239/34, 53, 55, 56, 57

(56) References Cited

U.S. PATENT DOCUMENTS

| 1,675,141 A | 6/1928 | Scholl |
|---|---|---|
| 2,545,801 A | 3/1951 | Wrazen |
| 2,573,625 A | 10/1951 | Swart |
| D196,639 S | 10/1963 | Irving |
| D275,784 S | 10/1984 | Reedman |
| 4,546,562 A | 10/1985 | Jones |
| D287,049 S | 12/1986 | Torres |
| 4,840,773 A | 6/1989 | Wade |
| 5,593,641 A | 1/1997 | Hornberger, Sr. |
| 5,816,951 A | 10/1998 | Hudock |
| 5,876,678 A | 3/1999 | Harrell et al. |
| D429,325 S | 8/2000 | Macaree |
| 6,103,201 A | 8/2000 | Green |
| D433,745 S | 11/2000 | Cowell |
| D434,260 S | 11/2000 | Rosenstadt et al. |
| 6,161,820 A | 12/2000 | Wu |
| 6,270,720 B1 | 8/2001 | Mandish |

Primary Examiner—Harold Joyce
(74) Attorney, Agent, or Firm—Dennis G. LaPointe

(57) ABSTRACT

A sports figure shaped fan for ventilation grills comprising a caricature formed in the shape of a sports figure. The fan is attached to a ventilation grill and the arms are extended and rotate when subjected to a back draft from the air flow of the ventilation system. The rotation mimics a throwing action of the sports figure. The fan also includes a reservoir and access to the reservoir for inserting one of a scenting agent, a deodorizing agent and a combination thereof, in the reservoir located in a designated portion of the caricature. The designated portion of the sports figure caricature is sufficiently permeable on either side of the reservoir so that a vapor is dispersed by the movement of the air flow. Another embodiment includes the lighting of a portion of the sports figure when a telecommunication signal is received by a cell phone.

14 Claims, 4 Drawing Sheets

AIR FRESHENER SPORTS FIGURE FAN FOR AIR VENTS

RELATED APPLICATION

This application is a continuation-in-part application of U.S. patent application Ser. No. 10/443,333 filed May 22, 2003 now U.S. Pat. No. 6,764,656.

FIELD OF INVENTION

The invention relates to a fan for an air vent that is formed in the shape of a sports figure and whose arms rotate to serve as fan blades with the device being capable of dispersing an aromatic scent for freshening an area, such as the personnel compartment of the vehicle or a room.

BACKGROUND OF INVENTION

There are air fresheners or deodorizers for automobiles that are formed in the shaped for various action figures such as the deodorizer disclosed in Design Pat. 196,639 to Irving, which hangs from any part of the interior compartment of a vehicle. Another air freshener is that disclosed in Design Pat. 287,049 to Torres, which is simply a thin card that hangs from any part of the interior compartment of a vehicle.

The Torres patent does disclose an imprint of a soccer player but there is no action associated with the sports figure. Similarly, there is no action associated with the caricature depicted in the Irving patent. As such, it simply hangs in the vehicle in a non-noticeable non-entertaining fashion.

SUMMARY OF THE INVENTION

The present invention provides the benefits of devices such as those mentioned above, in addition, to providing a fan like effect with the rotating arms that mimic a throwing action of a sports figure, such as a baseball player, a basketball player, a football player, and other sport caricatures that have a throwing action as part of the sport game.

Aromatic/deodorizing scents can be optionally incorporated into the device by addition of aromatic or deodorizing agents such as beads, wax or oil in absorbent material in a designated portion of the device, preferably the head portion of the device. Should the head portion be designated to contain the scent/deodorizing means, then access means to a small holding area or reservoir could be through an aperture at the top of the head, the face, a face visor, a face guard, a face mask, or the cap/helmet portion of the head. It is preferable that scenting means be something other than oils, although oils in an absorbent material would work. Preferably means such as beads or scented wax would be longer lasting and easier to market and use with the device. For example, if the sports figure is a football player, the helmet portion may be integral to the body portion but the visor or face mask may be removable to insert the aromatic and/or deodorizing pellets (beads), wax or oils. Another embodiment is the provision that the whole helmet portion is removable exposing a formed void within which, the aromatic and/or the deodorizing means may be inserted. Another access means is to provide an opening or aperture, such as a slotted area on top of the helmet. If the figure is a baseball player, then the face or cap may be removable to insert the scenting/deodorizing means, or again the aperture on top of the cap would work.

The device is attached by any of a variety of known means in the art, such as a clip, to the a ventilation grill, such as those on the dashboard of a motor vehicle. For example, this can be done with an attachment to the back body portion of the device using a clip or spring wire or other attachment means, that maintains the sports figure aligned in a generally vertical and parallel relationship with the grill face of the vehicle ventilation system. When the ventilation fan is turned on, the device is close enough to the ventilation grill face so that arms capture the air flow and rotate freely, that is, the arms are designed to capture the air flow to facilitate the rotation in such a way as to mimic a repetitive throwing action. Essentially, the arms are socketed within the shoulder socket of the caricature with rotating bearing means so as to rotate freely. Rotating bearing means may be concentric sleeves at the arm pivot point. The arms are typically relatively thin but with some depth or cross-width so as to be relatively realistic in form. The arms are typically angled slightly or cupped at a portion thereof to capture the flow of air and to activate the rotation for mimicking a forward throwing action or in a reverse pattern to mimic an underhand throwing action, such as by a softball pitcher.

When used in an automobile, it is anticipated that children in the vehicle will be fascinated by the sports figure arms rotating and at the same time, the air in the vehicle personnel compartment can be refreshed and/or deodorized.

Another entertaining feature incorporated in the invention as another embodiment, is the addition of a circuitry, including a microprocessor, that receives telecommunication signals, such those received by cellular phones, hereinafter referred to as "cell" phones. The circuitry can include a short wave non-transmitting receiver chip that is in electronic communication with an LED light that lights up when a telecommunication signal is being received by the cell phone. The LED bulb would preferably be placed within the caricature in such a location so as to make the head light up. Typically, the signal can be picked up within an approximate radius of about six (6) feet, depending on the strength of the short wave telecommunication signal being received by the cell phone. This would work very well within the compartment of an automobile.

DETAILED DESCRIPTION OF THE INVENTION

Figure 1:
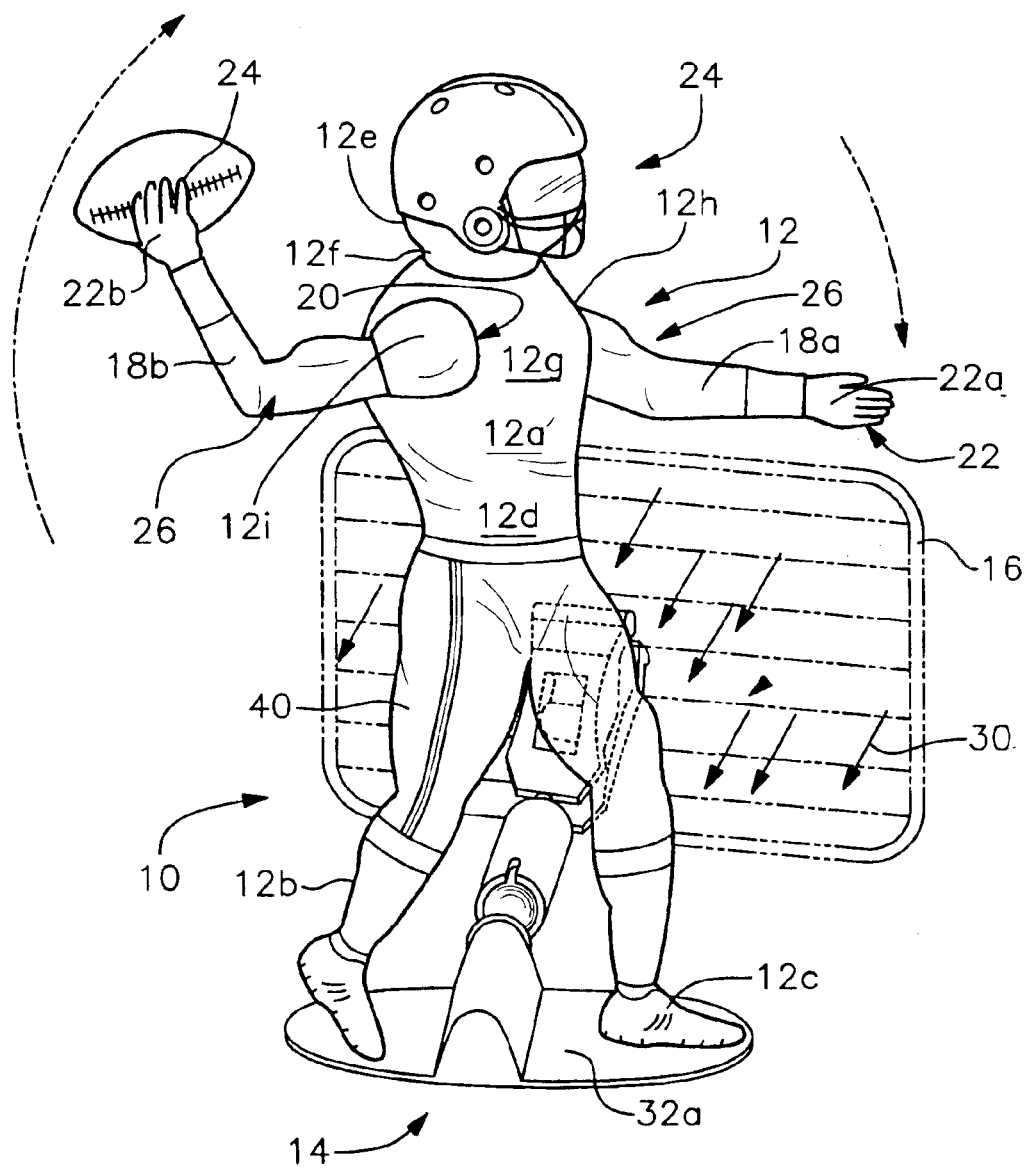
FIG. 1 is a representational perspective depiction of one embodiment of the invention, wherein a sports figure caricature representative of a football player throwing a football is shown attached to a ventilation grill face of an airflow system.

Referring now to the drawings, FIG. 1 discloses one embodiment of the present invention, which is depicted generally as 10. The invention is a sports figure shaped fan 10 for ventilation grills, such as grills 16 in dashboards of motor vehicles. The invention 10 comprises a caricature 12 formed in the shape of a sports figure. The caricature 12 includes a central body portion 12a, legs 12b and feet 12c depending from a lower torso portion 12d of the central body 12a and a head and neck portion, 12e,12f respectively, extending from an upper portion of the central body portion 12a. The central body portion 12a further defines and is representative of a lower torso 12d, chest area 12g and a respective left shoulder 12h and right shoulder 12i.

Figure 2:
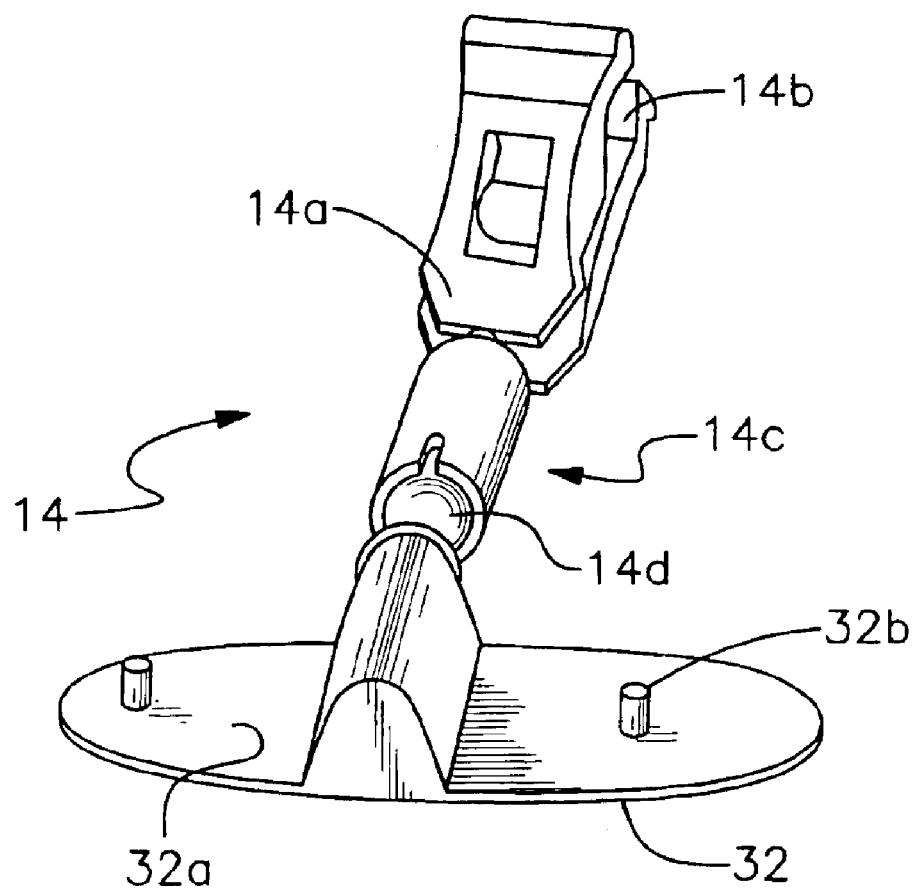
FIG. 2 is an example of one method of attaching the caricature of FIG. 1 to a ventilation grill face.

The invention 10 further includes means 14 for attaching caricature 12 to a ventilation grill 16. The device can in fact be attached to any fan grill system, and is not limited to installation in a vehicle grill 16. FIGS. 1 and 2 merely provide for one example of a preferred way of attaching the invention 10 to the grill 16. There are numerous other methods known in the art such as spring wire with bent ends, hooks, etc., that could be incorporated into the design depending on cost, practicality and preferences.

As shown in FIG. 1, the caricature 12 further includes two arms 18, each generally extended in such a way as to mimic a throwing action of a sports figure, the two arms representing respectively a left arm 18a and a right arm 18b, each attached to corresponding left shoulder 12h and right shoulder 12i. The two arms 18a,18b have means 20 for rotating about each respective left and right shoulders 12h, 12i. There are numerous ways known in the art to provide the rotating shoulder socket feature. It is sufficient to show the rotation of the arms by the arrows in FIG. 1 about the shoulder sockets. For example, the arms 18 may be socketed within the shoulder 12h, 12i socket of the caricature 12 with rotating bearing means so as to rotate freely. Rotating bearing means may be concentric sleeves at the arm pivot point.

As discussed above, when the ventilation fan is turned on, the device 10 is close enough to the ventilation grill 16 face so that arms 18 capture the air flow and rotate freely, that is the arms 18 are designed to capture the air flow to facilitate the rotation in such a way as to mimic a repetitive throwing action. Although not readily observable by the representational depiction of FIG. 1, the arms 18a, 18b are typically relatively thin but with some depth or cross-width so as to be relatively realistic in form. The arms 18a,18b are typically angled slightly or cupped at a portion thereof to capture the flow of air and to activate the rotation for mimicking a forward throwing action or in a reverse pattern to mimic an underhand throwing action, such as by a softball pitcher.

The artistic sculpturing of the caricature 12 in general, should be done so as to present a realistic image of a sports athlete, while maintaining a design on the arms 18a,18b so as to enhance the capturing of an air flow, thereby generating the mimicking of a throwing action by the rotation of the arms 18. One hand 22 (left 22a or right 22b) depicts the holding of an object 24 being thrown. In the example shown in FIG. 1, the mimicking of the throwing of a football (right hand 22b) is being shown, although the caricature 12 could be a baseball player throwing a baseball, or a basketball player throwing a basketball, etc.

As discussed above, the two arms 18 also have means 26 for capturing an air flow generated by activating a ventilation system, such as in a motor vehicle, so that air flows in a direction emanating from behind the sports figure, for creating a fanning rotation of the two arms 18a,18b, as shown by the arrows in FIG. 1, about the shoulders 12h,12i in a direction mimicking a throwing action of the sports figure. The air flow emanating from a grill 16 in a dashboard of an automobile is generally depicted by the arrows 30 shown in FIG. 1. Means 26 for capturing the air flow can be accomplished by having a slight curvature to each arm (typically along one edge) or having the arm angled in such a way that the arms, which act as fan blades, capture the air and initiate rotation.

At least a portion of the sports figure includes a representation of a sporting uniform 40 worn by such sports figure. For example, the caricature 12 may include representational football shoes, football pants, a football shirt and a football helmet painted or otherwise depicted on the respective feet, legs, central body portion and head of the caricature. In this representation, the depicted player may be mimicking the throwing of a football being held in one hand. If the sports figure is a baseball player, the uniform 40 would be a typical baseball uniform, including the shoes, with a baseball cap, and the hand would be holding a baseball with the fan motion depicting a pitcher throwing the ball. If the sports figure is a basketball player, then the ball may be a basketball and the uniform would be shirt and shorts and sneakers, typically worn by basketball players. In most cases, the throwing action would be simulated as an overhand throwing action. However, if a softball player is depicted, then the throwing action may be underhand, or counter-clockwise rotation for a right-handed softball pitcher.

Figure 3A:
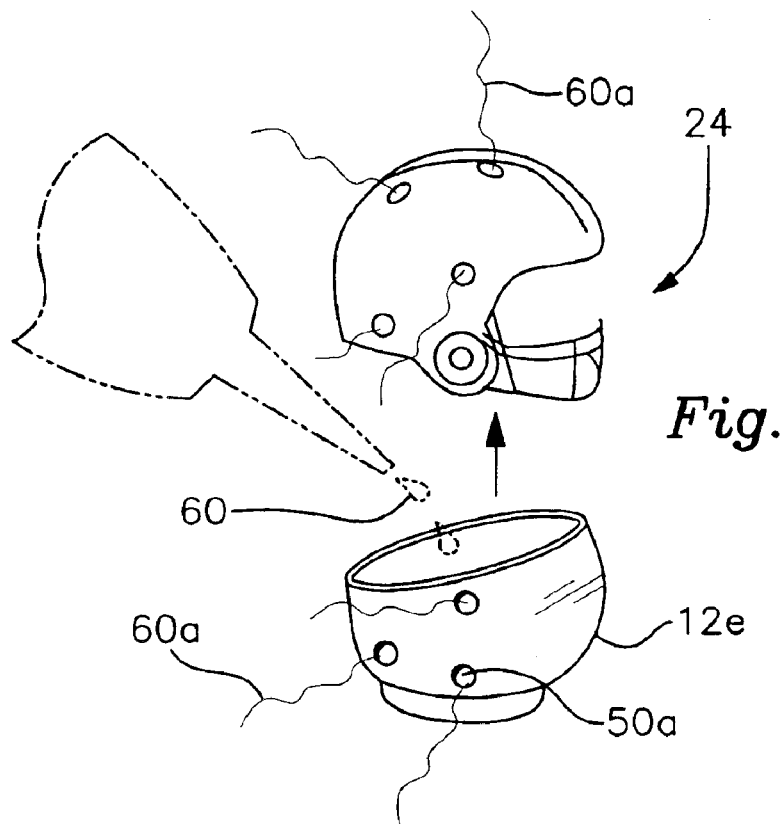
FIG. 3A is a schematic depiction of one example of a way of accessing a reservoir for the freshener/deodorizing agents, further specifically providing for the example, the insertion of oil drops into an absorbent pad (not shown)
Figure 3B:
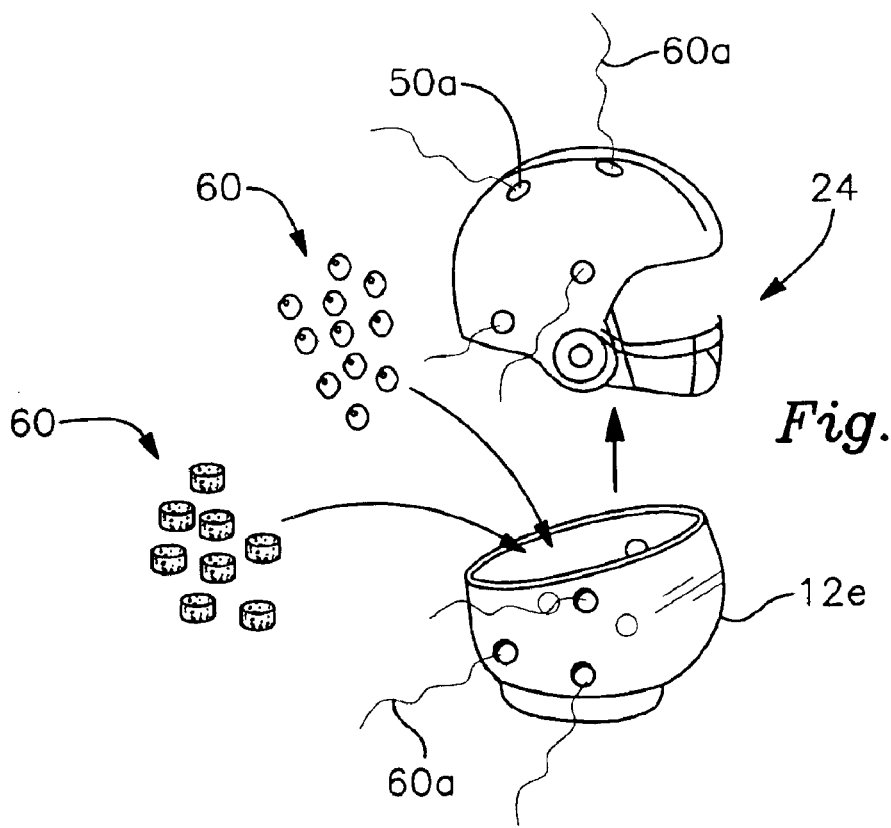
FIG. 3B is a schematic depiction of an alternative insertion of agents in the form of beads, granulars or blocks in the reservoir depicted in the example of FIG. 3A.

The invention 10 further includes access means 28 for inserting one of a scenting agent, a deodorizing agent and a combination thereof, in an interior reservoir 50 in a designated portion of the caricature 12. There are many means for doing this, some of which are fully described in co-pending U.S. patent application Ser. No. 10/443,333, filed May 22, 2003, which is incorporated by reference herein. That is, the reservoir 50 can almost be in any available convenient part of the caricature 12 and the reservoir can be any size and shaped as long as it contains the scenting agents, including pad and oils. FIGS. 3A and 3B merely depict one example of where the reservoir 50 may be located in the caricature 12, with FIG. 3A symbolically representing the insertion of scenting/deodorizing oils on an absorbent pad, which is not shown, but understood by one skilled in the art, and with FIG. 3B symbolically representing the insertion of other types of scenting/deodorizing agents. In FIGS. 3A and 3B, the helmet and face guard portion is shown removed to insert the agents 60 with the face visor remaining as part of the head portion 12e, however, the visor portion could have been part of the helmet and face guard portion as well. It is a matter of design preference on what depicted parts are removed to insert agents 60.

As discussed above, the agents are generally represented as 60 and may be in the form of beads or pellets, including wax (such as blocks, beads or pellets of wax), or in the form of oil absorbed or impregnated in an absorbent pad such as a cotton pad. The reservoir 50 serves as holding means for storing one of the scenting agent, the deodorizing agent and the combination thereof. The scenting agent and/or the deodorizing agent 60 effectively provides for means for air freshening and/or deodorizing an interior compartment of the motor vehicle or a room. The vapors released from the agents 60 are shown in FIGS. 3A and 3B as 60a.

The designated portion of the caricature 12 is sufficiently permeable on either side of the interior reservoir 50, as generally depicted by perforations 50a, so that when the air flow passes by the sports figure, a vapor 60a from the scenting/deodorizing agent 60, is dispersed by the movement of the air flow 30 emanating from the ventilation grill 16.

In one embodiment, the access means 28 for inserting scenting/deodorizing agents 60 in the reservoir 50, is an aperture 28a in the designated portion of the caricature 12. Although the reservoir 50 and its access means 28 could be located on any part of the caricature 12, it is preferred that the designated portion be the head portion 12e of the caricature 12. The upper head portion lends itself to be a good selection to incorporate the reservoir 50. Where an aperture 28a is desired, the aperture 28a can be located in the head portion 12e of the caricature 12, preferably the top.

As can be surmised, depending on the sports figure illustrated in the caricature 12, the head portion 12e may include a cap (for example, for a baseball player), a helmet (for example, for a football player), a face only (for example, for a basketball player), a face guard (for example, similar to those incorporated in football helmets), and a face visor (for example, similar to those worn in combination with the face guard of a football helmet) and any combination thereof. For example, the football player may have a depicted helmet and face guard only, therefore, a part of the face would typically be depicted. A baseball player may have a baseball cap and sunglasses or a face visor to imitate drop down sunglasses from the bill of a ball cap.

The head portion 12e or other caricature portion containing the reservoir 50, should be sufficiently permeable (50a) on either side of the interior reservoir 50 so that when the air flow 30 passes by the sports figure, a vapor 60a from the scenting/deodorizing agent 60 is dispersed by the movement of the air flow emanating from the ventilation grill 16.

The permeable feature 50a can be one of more apertures, including a single aperture or a plurality of finer apertures.

The means 20 for rotating the arms 18 about the shoulders 12h,12i can be provided in a number of ways known in the art. For example, a rotatable pin could be fixed to the arms and inserted through a tubular shaped bushing extending through the shoulders 12h,12i. A concentric bushing acting as a spacer between the arms 18 and shoulders 12h,12i would also typically be provided; and the pin, acting as an axis of rotation, can be designed with sufficient tolerance to rotate with relative ease when subjected to the back draft of the air flow.

The central body portion 12a, the head and neck portion 12e,12f respectively, the legs 12d and the arms 18 may be made from a variety of lightweight materials. For example, polymeric material or plastic based material may be used, cardboard stock material may be used, light-weight metallic material may be used and a combination of any of these materials may be used.

As shown in FIGS. 1 and 2, the means 14 for attaching the caricature 12 to the ventilation grill 16 is attached to a base portion 32 underlying the feet 12c of the caricature 12. A top surface 32a of the base portion 32 represents a surface on which the caricature 12 is standing. The means 14 for attaching the caricature 12 to the ventilation grill 16 can be made in a number of ways as discussed above but a preferred embodiment is the incorporation of a clip 14a having a gripping portion 14b at one end thereof for gripping a portion of the ventilation grill 16 and an engagement portion 32b on the base portion 32. Engagement portion 32b may be made in a number of ways known in the art; however, a recommended way is to provide pin-like features as shown in FIG. 2, where the pins engage receiving apertures (not shown) under the feet 12a of the caricature 12. In order to properly align the caricature, means 14c for adjusting the orientation of the caricature 12 relative to the ventilation air flow direction 30 are provided. The means 14c for adjusting the orientation of the caricature 12 relative to the ventilation air flow direction 30 can be provided in a number of ways known in the art. A preferred method is the inclusion of a ball and socket joint 14d as shown as an example in the drawings. Typically, these types of joints incorporate sufficient resistance or friction such that adjustments can be made relatively easy and the desired adjusted position is maintained after such adjustments.

Figure 4A:
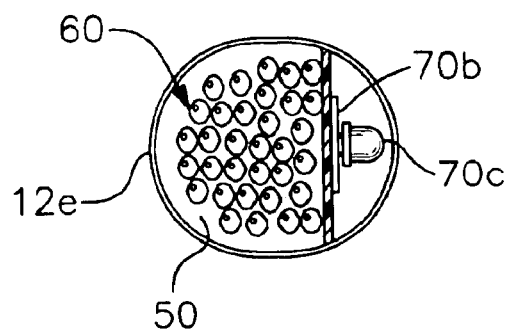
FIG. 4A is a schematic representation of an example of where an LED light could be located so as to make the head light up in one embodiment of the invention.
Figure 4B:
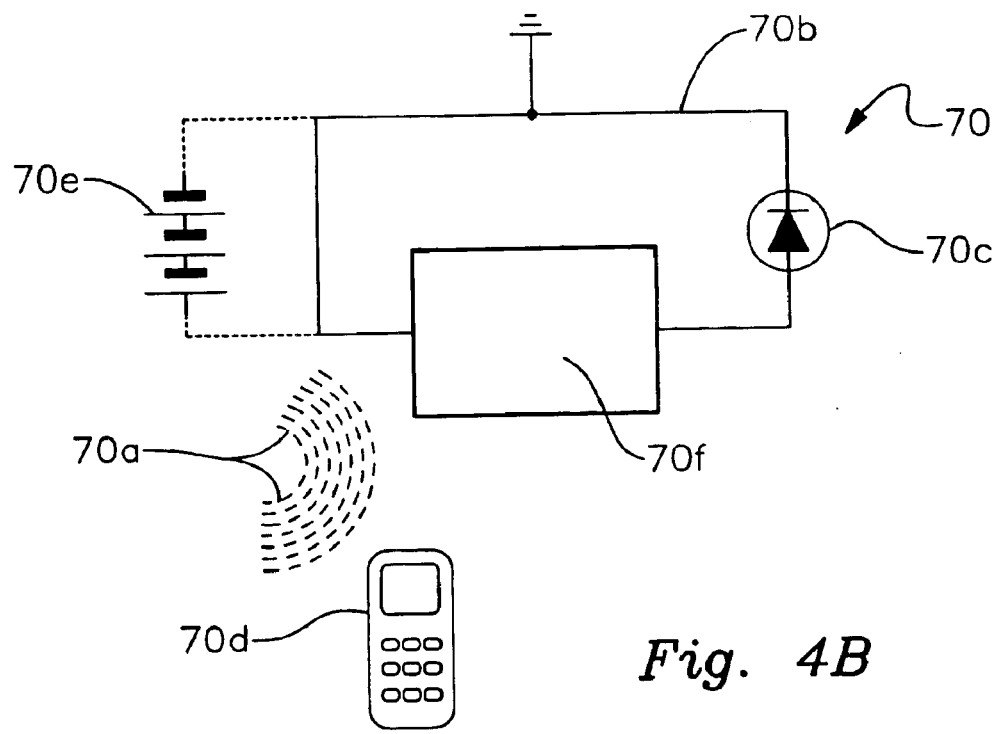
FIG. 4B is a generic schematic circuit to show that the concept of the circuitry being activated to light up an LED bulb when, for example, a cell phone receives telecommunication signals.

In still another embodiment of the invention 10, the caricature 12 may include means 70 for lighting a desired portion of the caricature 12. The means 70 for lighting up the desired portion of the caricature would have circuitry to receive telecommunication transmission signals 70a, which activate a circuit 70b that lights a lighting or illumination means 70c within the desired portion of the caricature 12. The illuminating means 70c is typically a LED bulb, as shown in the example of FIGS. 4A and 4B, however, with certain batteries, regular incandescent bulbs could be used like flashlight bulbs. The preference is the use of LED bulbs for compactness purposes. In FIG. 4A, the LED bulb 70c is shown located within the reservoir 50 of the head portion 12e. This is merely one example of where within the caricature 12 that the illumination means 70c may be located.

As shown in FIG. 4B, circuitry 70b may be designed to receive short wave or telecommunication transmission signals 70a typically received by a cell phone 70d.

As alluded to above and as conceptually depicted in FIG. 4B, the circuitry 70b can be powered by a separate battery in the circuitry 70b as shown by the phantom lined battery 70e, or the power on/off circuitry may be incorporated directly within the chip or microprocessor 70f, that also receives the signal 70a to activate the circuit. One skilled in the art of software programming and microprocessor circuitry can readily design such a circuit 70b that performs according to the operating parameters described above.

It should be understood that the preceding is merely a detailed description of one or more embodiments of this invention and that numerous changes to the disclosed embodiments can be made in accordance with the disclosure herein without departing from the spirit and scope of the invention. The preceding description, therefore, is not meant to limit the scope of the invention. Rather, the scope of the invention is to be determined only by the appended claims and their equivalents.

What is claimed is:

1. A sports figure shaped fan for ventilation grills comprising:

a caricature formed in the shape of a sports figure;

means for attaching the caricature to a ventilation grill;

the caricature further including two arms, the two arms representing respectively a left arm and a right arm attached to corresponding left and right shoulders of the caricature;

the two arms having means for rotating about each respective left and right shoulders of the caricature; and the two arms having means for capturing an air flow generated by activating a ventilation system so as to create an air flow emanating from behind the sports figure, and for creating a fanning rotation of the two arms in a direction mimicking a throwing action of the sports figure;

wherein at least a portion of the sports figure includes a representation of a sporting uniform worn by said sports figure.

2. The sports figure shaped fan according to claim 1, wherein
the caricature includes a central body portion, legs and feet, and a head and neck portion extending from an upper portion of the central body portion; and
the central body portion defines a representative lower torso, chest area and said left and right shoulders of the caricature.

3. The sports figure shaped fan according to claim 1, further comprising:
access means for inserting one of a scenting agent, a deodorizing agent and a combination thereof, in an interior reservoir in a designated portion of the caricature;
the reservoir being holding means for storing one of the scenting agent, the deodorizing agent and the combination thereof;
said one of the scenting agent, the deodorizing agent and the combination thereof providing means for one of air freshening, deodorizing and the combination of air freshening and deodorizing; and
the designated portion of the caricature being sufficiently permeable on either side of the interior reservoir so that when the air flow passes by the sports figure, a vapor from said one of the scenting agent, the deodorizing agent and the combination thereof, is dispersed by the movement of the air flow emanating from the ventilation grill.

4. The sports figure shaped fan according to claim 3, wherein the access means for inserting one of the freshener scenting agent, the deodorizing agent and the combination thereof in the reservoir, is an aperture in the designated portion of the caricature.

5. The sports figure shaped fan according to claim 4, wherein the aperture is located in a head portion of the caricature.

6. The sports figure shaped fan according to claim 1,
wherein a predetermined portion of a head portion of the caricature is temporarily removable to provide access to an interior reservoir serving as holding means for storing one of a scenting agent, a deodorizing agent and a combination thereof;
said one of the scenting agent, the deodorizing agent and the combination thereof providing means for one of air freshening, deodorizing and the combination of air freshening and deodorizing; and
the head portion being sufficiently permeable on either side of the interior reservoir so that when the air flow passes by the sports figure, a vapor from said one of the scenting agent, the deodorizing agent and the combination thereof, is dispersed by the movement of the air flow emanating from the ventilation grill.

7. The sports figure shaped fan according to claim 2, wherein the central body portion, the head and neck portion, the legs and two arms are made from material selected from the group comprising one of polymeric material, cardboard material, light-weight metallic material and a combination thereof.

8. The sports figure shaped fan according to claim 1, wherein the means for attaching the caricature to the ventilation grill is attached to a base portion underlying said caricature, a top surface of the base portion representing a surface on which the caricature is standing.

9. The sports figure shaped fan according to claim 8, wherein the means for attaching the caricature to the ventilation grill comprises:
a clip having a gripping portion at one end thereof for gripping a portion of the ventilation grill and an engagement portion on the base portion; and
means for adjusting an orientation of the caricature relative to the ventilation air flow direction.

10. The sports figure shaped fan according to claim 9, wherein the means for adjusting the orientation of the caricature relative to the ventilation air flow direction is a ball and socket joint.

11. The sports figure shaped fan according to claim 1, further comprising:
means for lighting a desired portion of the caricature, said means for lighting the desired portion of the caricature having circuitry to receive telecommunication transmission signals, which activate a circuit that activates an illumination means within the desired portion of the caricature.

12. The sports figure shaped fan according to claim 11, wherein the illumination means is a LED bulb.

13. The sports figure shaped fan according to claim 11, wherein the telecommunication transmission signals are received by a cellular phone.

14. The sports figure shaped fan according to claim 11, wherein the desired portion of the caricature that is illuminated is the head portion.

* * * * *